(12) United States Patent
Safonov et al.

(10) Patent No.: US 11,364,261 B2
(45) Date of Patent: Jun. 21, 2022

(54) ALLEVIATING COMMON COLD AND INFLUENZA SYMPTOMS WITH MOLECULAR HYDROGEN

(71) Applicant: H2 Universe, LLC., Granbury, TX (US)

(72) Inventors: Vladimir L. Safonov, Granbury, TX (US); Marina Yu Safonov, Granbury, TX (US)

(73) Assignee: H2 Universe, LLC, Granbury, TX (US)

( * ) Notice: Subject to any disclaimer, the term of this patent is extended or adjusted under 35 U.S.C. 154(b) by 0 days.

(21) Appl. No.: 16/526,280

(22) Filed: Jul. 30, 2019

(65) Prior Publication Data

US 2020/0030372 A1    Jan. 30, 2020

Related U.S. Application Data

(60) Provisional application No. 62/764,355, filed on Jul. 30, 2018.

(51) Int. Cl.
*A61K 47/26* (2006.01)
*A61P 31/16* (2006.01)
(Continued)

(52) U.S. Cl.
CPC ............ *A61K 33/06* (2013.01); *A61K 47/02* (2013.01); *A61K 47/10* (2013.01); *A61K 47/26* (2013.01); *A61P 31/16* (2018.01)

(58) Field of Classification Search
CPC .... A61K 31/519; A61K 31/522; A61K 31/44; A61K 31/444; A61K 31/506; A61K 31/713; A61K 33/06; A61K 31/337; A61K 31/513; A61K 31/5377; A61K 31/7068; A61K 33/16; A61K 33/44; A61K 31/5513; A61K 31/704; A61K 31/353; A61K 31/505; A61K 31/517; A61K 31/551; A61K 31/167; A61K 31/192; A61K 31/365; A61K 31/436; A61K 31/4436; A61K 31/538; A61K 31/5383; A61K 31/675; A61K 31/702; A61K 31/7105; A61K 31/07; A61K 31/137; A61K 31/155; A61K 31/164; A61K 31/166; A61K 31/19; A61K 31/203;
(Continued)

(56) References Cited

U.S. PATENT DOCUMENTS 8,852,660 B2   10/2014   Miljkovic
10,076,540 B1   9/2018   Perricone
(Continued)

OTHER PUBLICATIONS

Screen shot of Krucik, G., Acute upper respiratory infection, 2013, https://www.healthline.com/health/acute-upper-respiratory-infection#causes from The Wayback Machine (Year: 2013).*
(Continued)

*Primary Examiner* — Melissa L Fisher
*Assistant Examiner* — Ayaan A Alam
(74) *Attorney, Agent, or Firm* — Morgan, Lewis & Bockius LLP

(57) ABSTRACT

A method for alleviating, preventing or treating symptoms of a viral infection such as common cold and flu, comprising administering to a subject in need thereof at least one solid form that releases molecular hydrogen upon exposure to the subject's gastric juice.

11 Claims, 1 Drawing Sheet

(51) Int. Cl.
*A61K 33/06* (2006.01)
*A61K 47/10* (2017.01)
*A61K 47/02* (2006.01)

(58) Field of Classification Search
CPC .... A61K 31/232; A61K 31/335; A61K 31/36; A61K 31/439; A61K 31/4439; A61K 31/4745; A61K 31/4995; A61K 31/53; A61K 31/5395; A61K 31/546; A61K 31/555; A61K 31/573; A61K 31/7024; A61K 31/727; A61K 31/737; A61K 33/24; A61K 33/243; A61K 33/14; A61K 33/30; A61K 33/40; A61L 15/18; A61L 15/46; A61L 2300/102; C01F 11/181; C01F 11/158
See application file for complete search history.

(56) References Cited

U.S. PATENT DOCUMENTS

| | | | | |
|---|---|---|---|---|
| 2007/0110676 | A1* | 5/2007 | Clymer | A61K 31/192 424/45 |
| 2013/0034542 | A1* | 2/2013 | Ganter | A61K 38/40 424/130.1 |
| 2013/0323190 | A1 | 12/2013 | Ohta et al. | |
| 2015/0258136 | A1* | 9/2015 | Lucas | A61P 17/04 424/600 |
| 2018/0092816 | A1 | 4/2018 | Perricone et al. | |

OTHER PUBLICATIONS

Wang, H., Ma, S., The cytokine storm and factors determining the sequence and severity of organ dysfunnction in multiple organ dysfunction syndrome, 2008, American Journal of Emergency Medicine, 26, 711-715 (Year: 2008).*

Wat, D., The common cold: a review of the literature, (2004), European Journal of Internal Medicine, 15, 79-88 (Year: 2004).*

Purative, Active H2 Ultra Molecular Hydrogen 460mg, 60 Tablets, 2015, Amazon.com, screenshot of https://www.amazon.com/Purative-Active-Molecular-Hydrogen-Tablets/dp/B07D7RD7VT (Year: 2015).*

Huang, et al., "Recent advances in hydrogen research as a therapeutic medical gas," Free Radical Research, 44(9): Sep. 2010, pp. 971-982.

Ohta, "Recent Progress Toward Hydrogen Medicine: Potential of Molecular Hydrogen for Preventive and Therapeutic Applications," Current Pharmaceutical Design, 17, 2011, pp. 2241-2252.

Safonov, et al., "Hydrogen nanobubbles in a water solution of dietary supplement," Colloids and Surfaces A: Physicochemistry Engineering Aspects, vol. 436 (2013), pp. 333-336.

Lucas, et al., "Molecular mechanisms underpinning laser printer and photocopier induced symptoms, including chronic fatigue syndrome and respiratory tract hyperresponsiveness: pharmacological treatment with Cinnamon and Hydrogen," Neuroendrocrinology Letters, vol. 34, No. 8, pp. 723-737, 2013.

Lucas, et al., "Role of the Toll Like Receptor (TLR) Radical Cycle in Chronic Inflammation: Possible Treatments Targeting the TLR4 Pathway," Mol. Neurobiol., vol. 48, pp. 190-204, 2013.

* cited by examiner

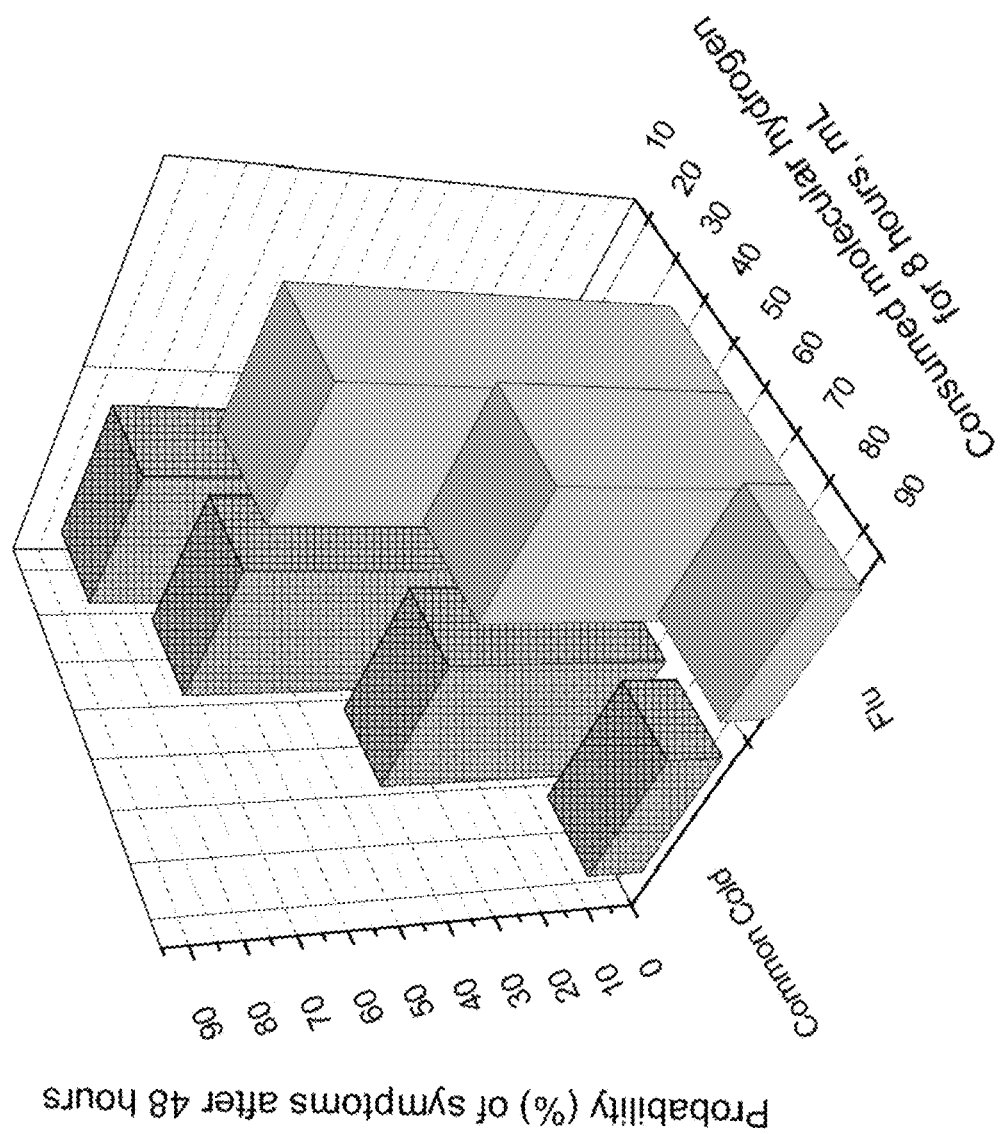

ALLEVIATING COMMON COLD AND INFLUENZA SYMPTOMS WITH MOLECULAR HYDROGEN

CROSS REFERENCE TO RELATED APPLICATIONS

This application claims the benefit of priority to U.S. Provisional Patent Application No. 62/764,355, filed Jul. 30, 2018, the entire contents of which are hereby incorporated by reference.

TECHNICAL FIELD

The present disclosure relates to prevention, treatment, and alleviation of symptoms of viral infections such as common cold and influenza using molecular hydrogen.

BACKGROUND

Hydrogen therapy includes the use of molecular hydrogen ($H_2$) for treatment and prevention of various conditions and diseases. Basic and clinical research has revealed that $H_2$ is an important physiological regulatory factor with antioxidant, anti-inflammatory and anti-apoptotic protective effects on cells and organs. See Huang et al., Recent advances in hydrogen research as a therapeutic medical gas, Free Radical Res. 44(9) (2010): 971-82; Ohta, Recent progress toward hydrogen medicine: potential of molecular hydrogen for preventive and therapeutic applications. Curr Pharm Des. 17(22) (2011): 2241-52. Hydrogen-based therapy is a rapidly growing area.

Existing methods for delivering of molecular hydrogen to a patient's body include administration of $H_2$ inhalations, injecting $H_2$-containing solutions, oral administration of hydrogen-infused liquids (e.g., $H_2$-enriched water), and other ways of delivering hydrogen to the subject's body. Each of the existing approaches has its benefits and disadvantages. For example, $H_2$ inhalations and injections are applicable only in clinical settings. $H_2$-infused liquids may be not stable since hydrogen tends to dissipate quickly, which can affect efficacy of the liquid. Furthermore, benefits and potential of $H_2$ for the human are still being investigated.

Accordingly, there is a need to novel approaches to treatment of various conditions using $H_2$.

SUMMARY OF THE INVENTION

Accordingly, in various aspects, compositions and methods for administering molecular hydrogen ($H_2$) in a consumable solid form to a subject are provided. The solid $H_2$-generating forms, such as, for instance, capsules, tablets or pills, are administered orally and, when reaching the subject's gastrointestinal tract, release $H_2$ upon contact with the gastric juice that includes hydrochloric acid.

In some aspects, compositions and methods are provided for prevention, treatment, and alleviation of symptoms of viral infections such as, e.g., common cold, influenza, or acute upper respiratory infection, by orally administering to a subject in need thereof a solid $H_2$-generating form capable of generating $H_2$ in the subject's gastrointestinal tract. The subject that is administered the $H_2$-generating form is in need of prevention or alleviation of viral infection symptoms—i.e. the subject is afflicted by early symptoms of an infection, is at an increased risk for infection, and/or has not been exposed to an infectious agent. The molecular hydrogen can be generated in the stomach as hydrogen nanobubbles, which can be stable for several hours. Hydrogen nanobubbles penetrate through the body tissues and blood, and provide therapeutic effect such that boosting the subject's immune response to a viral infection. The compositions have no known side effects and can be self-administered.

In embodiments, the present methods involve dosing at the onset of symptom presentation to mitigate symptom severity and/or duration. In embodiments, the present methods involve dosing at the onset of symptom presentation to prevent the onset of further symptoms.

BRIEF DESCRIPTION OF THE DRAWINGS

Non-limiting embodiments of the present invention will be described by way of example with reference to the accompanying figures, which are schematic and are not intended to be drawn to scale. The drawings illustrate exemplary embodiments of the invention and do not therefore limit its scope. In the figures, each identical or nearly identical component illustrated is typically represented by a single numeral. For purposes of clarity, not every component is labeled in every figure, nor is every component of each embodiment of the present disclosure shown where illustration is not necessary to allow those of ordinary skill in the art to understand the present disclosure. In the figures:

FIG. 1 is a diagram illustrating efficacy of the methods and compositions in accordance with some embodiments for alleviating symptoms of common cold and flu.

DETAILED DESCRIPTION

The present disclosure provides methods and compositions for oral administration of hydrogen-generating solid forms that generate molecular hydrogen ($H_2$) upon contact with the interior of the subject's gastrointestinal tract. The solid dietary forms (e.g., tablets, pills, capsules, beads, pellets, granules, powder, sachets, jell, etc.) are formulated such that they are safely ingestible and, once ingested, release $H_2$ in the amount that is sufficient to deliver a therapeutic effect. The therapeutic effect can be prevention, alleviation, or treatment of symptoms of common cold, flu, or other viral infections (e.g., acute upper respiratory infection).

Molecular hydrogen is a known antioxidant that is also capable of providing anti-inflammation effect. The effect of $H_2$ treatment was reported in oxidative stress-related disease. For example, studies revealed that intraperitoneal injection of hydrogen-rich saline has anti-inflammation, anti-oxidant, anti-apoptotic effects and protected organism against polymicrobial sepsis and acute peritonitis injury both by reducing oxidative stress and via decreasing mass proinflammatory responses. See Yang et al., Hydrogen Medicine Therapy: An Effective and Promising Novel Treatment for Multiple Organ Dysfunction Syndrome Induced by Influenza and Other Viral Infections Diseases? SOJ Microbiology and Infection Diseases (2017), vol. 5(2):1-6. Yang et al. suggest using injections of hydrogen-rich saline solutions. U.S. Pat. No. 9,522,250 describes using a hydrogen-rich gas mixture safe for inhalation by patients suffering from viral or bacterial pneumonia. When using this method, many precautions must be followed, since molecular hydrogen, together with molecular oxygen in the atmosphere, has a high explosive potential. For this reason, inhalation approaches are only applicable in stationary conditions in controlled facilities.

Accordingly, in some aspects of the present disclosure, methods and compositions for preventing, alleviating, and/or treating symptoms of viral infections, such as common cold and influenza, are provided which involve oral administration of ingestible hydrogen-generating solid forms. The described approach is safe and suitable for administration in any setting, including clinical setting and for self-administration.

It has been suggested that the majority of viral-induced symptoms in a person are caused not by a virus itself but by an inflammatory cytokine storm and oxidative stress which promote each other and induce so called Multiple Organ Dysfunction Syndrome. Therefore, suppression of the cytokine storm and reduction of oxidative stress can significantly alleviate the symptoms of influenza. See Mishra et al., Emerging avian influenza infections: Current understanding of innate immune response and molecular pathogenesis. Int. Rev. Immunol. (2017), 36(2):89-107; Oliveira et al., Catalase protects *Aedes aegypti* from oxidative stress and increases midgut infection prevalence of Dengue but not Zika. PLoS neglected tropical diseases (2017), 11(4): e0005525; Zhu et al., Qiangzhi decoction protects mice from influenza A pneumonia through inhibition of inflammatory cytokine storm. Chin. J. Integr. Med. (2015), 21(5):376-383.

Accordingly, the present invention provides methods that make use of $H_2$-generating solid forms that boost the subject's immune response to a viral infection rather than directly affect (e.g., weaken) the virus. The experiments conducted by the inventors demonstrate that the molecular hydrogen therapy in accordance with some embodiments of the present disclosure effectively suppresses Multiple Organ Dysfunction Syndrome induced by influenza viruses, with molecular hydrogen acting as effective antioxidant and anti-inflammatory agent.

The described methods and compositions involve administration of an $H_2$-generating composition, in the form of solid forms such as, e.g., capsules, pills, tablets, or compressed powder, to prevent, alleviate, and treat symptoms of viral infections such as common cold and influenza. The ingestion of such solid forms substantially increases the body's resistance to these viral infections. It should be noted that the present methods and compositions are not intended to treat a viral disease, but are rather developed for boosting the body's immune response within the first 48 hours from the onset of symptoms consistent with common cold or influenza. Thus, if, despite the subject's being administered a regimen of the present solid forms, within about 48 hours of their onset, the symptoms have not significantly subsided or disappeared, an antiviral or another medication should be administered (which may require a consultation with a medical professional).

As previously demonstrated, molecular hydrogen can form nanobubbles in a solution (e.g., a water solution). See Safonov and Khitrin, Hydrogen nanobubbles in a water solution of dietary supplement. Colloids and Surfaces A: Physicochemistry Engineering Aspects (2013), vol. 436: 333-336, which is incorporated by reference herein in its entirety. In the form of nanobubbles, $H_2$ easily penetrates through the walls of the stomach and reaches the bloodstream, thereby providing a desired therapeutic effect.

Accordingly, in some embodiments, a subject in need thereof is administered one or more $H_2$-generating solid forms that generate (e.g., as a result of a chemical reaction) and/or release stored $H_2$ upon contact with the hydrochloric acid (and/or other liquids) in the subject's gastrointestinal tract. The generated $H_2$ can be in the form of nanobubbles, as described in Safonov and Khitrin (2013), which facilitates $H_2$ penetration into tissues and organs, thereby boosting the subject's immune system.

In some embodiments, a method for preventing or treating symptoms of a viral infection comprises administering one or two capsules or other forms upon an onset of symptom(s) of a viral infection. The capsules, upon being ingested by a subject, generate at least 20 milliliters (mL) of $H_2$ in the gastric juice. The generated $H_2$ molecule penetrates through the walls of the stomach into the blood and acts as antioxidant and anti-inflammatory agent, thereby suppressing Multiple Organ Dysfunction Syndrome. In this way, the molecular hydrogen assists the subject's body with fighting the viral infection.

In some embodiments, one or more solid forms are administered to a subject within 48 hours from the onset of symptoms of a viral infection in the subject. The solid forms can be administered immediately upon the onset of one or more symptoms, within a few hours, or within 24 to 48 hours from the onset of the symptoms. The subject is in need of prevention, alleviation or treatment of symptoms of a viral infection—i.e. the subject is afflicted by early symptoms of an infection, is at an increased risk for infection (e.g., the subject has had a higher exposure to infectious agent than usual, etc.), and/or has not been exposed to an infectious agent, e.g., the subject has not had the flu or cold during the cold season, has not been vaccinated against the infectious agent or the vaccine is ineffective, or the subject has not been exposed to the infection agent for other reasons.

In various embodiments, the present methods treat, alleviate, or prevent the common cold, or symptoms thereof, where the etiology is, or relates to a viral infection. For instance, the virus can include one of more of rhinoviruses, adenoviruses, RSV, human parainfluenza viruses, metapneumovirus, coronaviruses, enteroviruses, respiratory syncytial viruses, influenza viruses (e.g., A and/or B) and parainfluenza viruses (e.g., type 1, type 2, and/or type 4).

In various embodiments, the present methods treat, alleviate, or prevent an upper respiratory infection.

Common cold symptoms may include, without limitation: stuffy, runny nose; scratchy, tickly throat; sneezing; watering eyes; low-grade fever; sore throat; mild hacking cough; achy muscles and bones; headache; mild fatigue; chills; and/or watery discharge from nose that thickens and turns yellow or green. Colds usually start 2 to 3 days after the virus enters the body. If left untreated (or sometimes even with a treatment), common cold symptoms may last from several days to several weeks.

Influenza (flu) symptoms may include, without limitation: cough, often severe; extreme exhaustion; fatigue for several weeks; headache; high fever; runny or stuffy nose; severe aches and pains; sneezing at times; a sore throat; and/or vomiting and diarrhea. Fever and body aches often last for 3 to 5 days, and cough and fatigue may last for 2 weeks or more.

In various embodiments, the occurrence and severity of symptoms treated by the present methods are measured according to the modified Jackson criteria (Jackson et al., Arch. Intern. Med., 101:267-78 (1958), which is herein incorporated by reference in its entirety).

In various embodiments, the occurrence and severity of symptoms treated by the present methods are measured according to a Wisconsin Upper Respiratory Symptom Survey (WURSS), an evaluative illness-specific quality of life instrument, designed to assess the negative impact of acute upper respiratory infection, presumed viral (the common cold). For instance, any of the Long (WURSS-44), short (WURSS-21 or WURSS-11), WURSS-24, and WURSS-K (for children) may be used (see, Journal of Family Practice 51(3):265, Journal of Clinical Epidemiology. 58 (6):609-617, 2005, European Respiratory Journal 28 (2):358-363, 2006, Qual. Life Res. 17 (1):75-85, 2008, and Health and Quality of Life Outcomes 7 (76), 2009, the entire contents of which are herein incorporated by reference).

In embodiments, the present methods relate to the treatment or prevention of one or more of the symptoms of a common cold of Table 1 below. For instance, in embodiments, the methods cause a reduction in symptoms or severity of symptoms from severe to moderate, or severe to mild, or severe to none, or moderate to mild, or moderate to none, or mild to none.

In embodiments, the present methods relate to the treatment or prevention of 1, or 2, or 3, or 4, or 5, or 6, or 7, or 8, or 9, or 10, or 11 of the symptoms of a common cold of Table 1 below.

In various embodiments, the present methods relate to prevention of one or more of the symptoms of a common cold of Table 1 below from progressing from none or mild to moderate or severe (e.g., none to mild, none to moderate, none to severe, mild to moderate, or mild to severe).

prevention of one or more related diseases, such as sinusitis, otitis, influenza, and infectious exacerbations of chronic obstructive pulmonary disease (COPD).

In various embodiments, the present methods reduce the volume of mucus secretion in the sinus cavity and/or reduce the viscosity of mucus in the sinus cavity. In various embodiments, the present methods provides for restoration of effective nasal mucociliary clearance function. In embodiments, the present methods lead to decreased accumulation of mucus within the nasal passages. In embodiments, the present methods lead to decreased nasal mucus production, e.g., decreased nasal mucus weight (e.g., total mucus weight less than 10 g, or 9 g, or 8 g, or 7 g, or 6 g, or 5 g, or 4 g, or 3 g, or 2 g, or 1 g). In embodiments, the present methods reduce the nasal mucociliary clearance time in the subject.

A subject may be administered the solid forms in accordance with the present disclosure after being diagnosed with or suspected for having a viral infection. The subject may self-diagnose the viral infection, and the solid forms may be self-administered.

The one or two capsules may be administered repeatedly, about every two hours. In some embodiments, the one or two

TABLE 1

| Symptom | None | Mild | Moderate | Severe |
|---|---|---|---|---|
| Sneezing | No sneezes | Few short episodes of sneezing | Occasional sneezes | Frequent sneezes |
| Runny Nose | No runny nose | Had to wipe nose (or blow) nose rarely | Had to wipe(or blow) nose occasionally | Had to wipe(or blow) nose frequently |
| Nasal congestion | No congestion | Breathing through nose slightly | Breathing through nose noisy, has "nasally" speech, breathes through mouth some | Breathes through mouth almost all the time because of nasal congestion, speech very "nasally" |
| Cough | No cough | Few short episodes of coughing | Occasional coughs or rare episodes of prolonged coughing | Frequent coughs or at least occasional episodes of prolonged coughing |
| Feverishness | No fever or looking flushed | Felt warm to the touch, no flushing | Felt very warm to the touch or temperature > 100.5°, slightly flushed | Felt hot to the touch or temperature > 102°, very flushed |
| "malaise" | No ill appearance or behavior | Slightly less active than normal | Activity reduced somewhat, not engaging in usual activities | Mostly in bed or lying down |
| Chilliness | No chilliness | Complaining about being cold, no extra clothing or blankets | Wearing extra clothes or using blanket to keep warm, | Very chilled, shivering, constantly under a blanket to keep warm |
| Headache | No headache | Mild Complaints of headache, no change in activity | Frequent complaints of headache, not as active because of headache | Mostly in bed because of headache |
| Myalgias | No muscle aches | Infrequent complaint of muscle aches or pains | Occasional complaint of muscle aches or pains | Frequent complaint of muscle aches or pains |
| Sore throat | No sore throat | Mild pain with swallowing | Moderate pain with swallowing | Very painful to swallow |
| "scratchy" throat | No throat pain | Infrequent complaint of pain in mouth or throat, discomfort mild | Occasional complaint of pain in mouth or throat, or moderate discomfort | Frequent complaint of pain in mouth or throat, or severe discomfort |
| Hoarseness | No change in voice | Speech is slightly hoarse or "husky" | Speech is very hoarse or "husky" | Cannot speak above a whisper because or hoarseness |

In various embodiments, in addition or alternative to the treatment of the common cold, or symptoms thereof, the present methods find use in the treatment, alleviation, or capsules may be administered four or five times, about every two hours after the onset of symptoms of a viral infection. Each dose of the capsule(s) produces at least 20 mL of $H_2$, which can be sufficient to reduce or eliminate the symptoms of the viral infection. As referred to herein, the volume of $H_2$, in mL, is a volume of $H_2$ at room temperature 20° C. (68 F) and atmospheric pressure at sea level. Under these conditions, for example, 10 mL of $H_2$ corresponds to a mass of 0.83 mg of molecular hydrogen. The total daily dose of $H_2$, which is administered to a subject in need hereof upon the onset of symptoms of a viral infection, can be at least about 6.6 mg (about 80 mL) of $H_2$. For comparison, in order to obtain approximately the same amount of hydrogen from hydrogen-saturated water, a person would need to consume at least 4-5 liters of hydrogen-rich water during one day. Also, the hydrogen-saturated water needs to be consumed right away after preparation, since the hydrogen evaporates quickly and the water loses it is efficacy.

In some embodiments, the dose of the composition is selected such that at least 6.6 mg (about 80 mL) of $H_2$ is generated in the subject's body over a period of about 8 hours when the compound is administered to the subject at least two times over that period.

Various amounts of $H_2$ may be administered in accordance with embodiments of the present disclosure. In some embodiments, the amount of $H_2$ used is about 0.5-15 mg, or about 1-15 mg, or about 1-10 mg, or about 1-7 mg, or about 1-5 mg, or about 3-15 mg, or about 3-10 mg, or about 3-7 mg, or about 3-5 mg, or about 5-15 mg, or about 5-10 mg, or about 5-7 mg, or about 7-15 mg, or about 7-10 mg, or about 8-10 mg, or about 1-15 mg. In some embodiments, the amount of $H_2$ used is about 8-10 mg. In embodiments, the amount of $H_2$ used is about 6-7 mg.

In some embodiments, the amount of $H_2$ used is about 4 mg, or about 5 mg, or about 6 mg, or about 7 mg, or about 8 mg, or about 9 mg, or about 10 mg. In some embodiments, the amount of $H_2$ used is about 7 mg. In some embodiments, the amount of $H_2$ used is about 6.5 mg. In some embodiments, the amount of $H_2$ used is about 6 mg. In some embodiments, the amount of $H_2$ used is about 6.65 mg.

In some embodiments, a single or unit dose includes $H_2$ in the amount of about 0.8 mg, or about 0.9 mg, or about 1 mg, or about 1.1 mg, or about 1.2 mg, or about 1.3 mg, or about 1.4 mg, or about 1.5 mg, or about 1.6 mg, or about 1.7 mg, or about 1.8 mg, or about 1.9 mg, or about 2.0 mg.

In some embodiments, the total dose of $H_2$ is about 1.6 mg, or about 1.8 mg, or about 1.9 mg, or about 2.0 mg, or about 2.1 mg, or about 2.2 mg, or about 2.3 mg, or about 2.4 mg, or about 2.5 mg, or about 2.6 mg, or about 2.7 mg, or about 2.8 mg, or about 2.9 mg, or about 3 mg, or about 3.1 mg, or about 3.2 mg, or about 3.3 mg, or about 3.4 mg, or about 3.5 mg, or about 3.6 mg, or about 3.7 mg, or about 3.8 mg, or about 3.9 mg, or about 4 mg.

In some embodiments, a total dose of $H_2$ is about 1.6 mg, or about 2.08 mg, or about 2.49 mg, or about 2.91 mg, or about 3.32 mg. The total dose can be a daily dose or it can be a dose delivered over a period of about 8 hours. Depending on the amount of the single dose, the composition can be administered two or more times (e.g., three, four, five, or six times) over a period of about 8 hours after the onset of common cold or influenza symptoms, or symptoms of another viral infection. In some embodiments, the total daily dose of $H_2$ is at least 7.0 mg (85 mL), at least 7.4 mg (90 mL), at least 7.8 mg (95 mL), or at least 8.3 mg (100 mL).

In some embodiments, a total dose of about 6.6 mg of $H_2$ (which corresponds to about 80 mL of $H_2$) can be used for an adult subject, e.g., an adult subject having a weight of about 80 kg. The dosage of the compositions can depend on various factors, including a severity of the condition, and the age, weight, and health of the subject to be treated. For example, subjects having a smaller weight can be administered the composition less frequently or at smaller doses, and subjects having a larger weight can be administered the composition more frequently or at larger doses. Some variations in the dosage can be expected.

In addition, it should be appreciated that, in some embodiments, the period during which the composition is administered is longer than 8 hours. Because the compositions in accordance with the present disclosure are safe for mammal (e.g., human) consumption, they can be administered as frequently as needed, though the recommended dosage is two to five times every two hours.

In some embodiments, the amount of the compositions described herein or their pharmaceutically acceptable salts are admixed with the carrier materials to produce a single dosage that can vary depending upon the subject being treated. In vitro or in vivo assays can be employed to help identify optimal dosage ranges.

The solid form in accordance with embodiments of the present disclosure can be administered to the subject in a dry form such that the solid form is not previously diluted in water or other liquid. The solid form can generate $H_2$ in the subject's stomach in various ways, each of which is safe for the subject. The solid form does not have any known side effects. In some embodiments, the solid form is formulated as an ingestible dietary product that is able to generate a therapeutically effective amount of $H_2$ in the gastric juice in a single dose. In some embodiments, the therapeutically effective amount of $H_2$ is at least 10 mL (0.83 mg), at least 11 mL (0.91 mg), at least 12 mL (1.00 mg), at least 13 mL (1.08 mg), at least 14 mL (1.16 mg) at least 15 mL (1.25 mg), at least 16 mL (1.33 mg), at least 17 mL (1.41 mg), at least 18 mL (1.50 mg), at least 19 mL (1.58 mg), or at least 20 mL (1.66 mg) generated by a single dose of the solid form.

The solid form can be consumed repeatedly, e.g., at least two times and up to 5 times, within a relatively short period of time. For example, in some embodiments, the solid form is first administered upon the onset of symptoms of a viral infection, and then repeatedly administered about every 2 hours. The solid form may be administered two, three, four, or five times. In some embodiments, in which the solid form generates a therapeutically effective amount of $H_2$ of about 10 mL (0.83 mg), two solid forms are administered as a single dose. Furthermore, in some embodiments, the solid form(s) can be administered more than five times. In some embodiments, a total dose of $H_2$ is about 1.6 mg, or about 2.08 mg, or about 2.49 mg, or about 2.91 mg, or about 3.32 mg.

In some embodiments, a method of treating or preventing symptoms of a viral infection is provided that comprises administering a plurality of ingestible hydrogen-generating solid forms to a subject experiencing symptoms of a viral infection, wherein each of the plurality of solid forms is configured to release at least 0.8 mg of molecular hydrogen upon exposure to the gastric juice of the subject.

The hydrogen-generating solid forms can be administered in various doses. For example, in some embodiments, the method generates at least 10 mL (0.83 mg) of molecular hydrogen upon exposure to the gastric juice of the subject.

In some embodiments, each of the plurality of solid forms comprises at least 1.2 mg of molecular hydrogen. In some embodiments, each of the plurality of solid forms comprises at least 1.6 mg of molecular hydrogen.

In some embodiments, the administering comprises administering two solid forms of the plurality of solid forms approximately every two hours. The plurality of solid forms can be administered to deliver at least 3 mg, at least 4.5 mg, or at least 6.5 mg of molecular hydrogen to the subject. In some embodiments, the plurality of solid forms are administered to deliver from about 6.5 mg to about 8.5 mg of molecular hydrogen to the subject.

In some embodiments, the administering comprises administering two solid forms of the plurality of solid forms approximately every two hours. The plurality of solid forms can be administered to deliver at least 1.6 mg, or at least 3.3 mg, or at least 5 mg, or at least 6.6 mg of molecular hydrogen to the subject. In some embodiments, the plurality of solid forms are administered to deliver from about 6.6 mg to about 8.30 mg of molecular hydrogen to the subject. In some embodiments, the plurality of solid forms are administered to deliver about 6.64 mg of molecular hydrogen to the subject, which can be done over a period of, for example, 8 hours.

The hydrogen-generating solid forms can be administered to the subject with various frequency, which is, in some embodiments, one or more solid forms about every two hours. For example, in some embodiments, the plurality of solid forms are administered at least two times over a period of about 8 hours.

In some embodiments, the plurality of solid forms are administered to the subject in a dry form, and the solid forms are not dissolved in water or another liquid prior to being administered.

As shown in the experiments described below, the inventors demonstrated that the solid forms in accordance with the present disclosure dramatically reduce the symptoms of a viral infection, such as common cold or influenza (flu). For example, in some embodiments, the described methods of administering the hydrogen-generating forms comprise reducing a probability of symptoms of the viral infection by at least 10%, at least 20%, at least 30%, at least 40%, at least 50%, at least 60%, at least 70%, at least 80%, or at least 90% after 48 hours of the beginning of the administration of at least one of the hydrogen-generating solid forms. In some embodiments, the symptoms become not detectable after several doses of the hydrogen-generating solid forms. The described methods allow treating or preventing various symptoms of viral infections (e.g., common cold and influenza) and can treat or prevent Multiple Organ Dysfunction Syndrome. In some embodiments, the symptom of the viral infection is an acute upper respiratory infection. In some embodiments, the symptoms of the viral infection are selected from one or more of those of Table 1 above. In some embodiments, the viral infection is an infection by one or more of rhinoviruses, adenoviruses, RSV, human parainfluenza viruses, metapneumovirus, coronaviruses, enteroviruses, respiratory syncytial viruses, influenza viruses (e.g., A and/or B) and parainfluenza viruses (e.g., type 1, type 2, and/or type 4).

In some embodiments, the solid form is in the powder form and it can include a unit dose comprising about 1 mg of molecular hydrogen and about 9.2 mg of magnesium oxide. Other ingredients can be included as well, non-limiting examples of which include microcrystalline cellulose, maltodextrin xanthan gum, citric acid, magnesium stearate, gelatin, and a coloring agent.

In some embodiments, the solid form is in the powder form and, optionally, it can include a unit dose comprising, e.g., about 1 mg of molecular hydrogen (or another amount), and, optionally, the powder does not include metallic magnesium or is substantially devoid of metallic magnesium. In such embodiments, $H_2$ molecules (e.g., in the form of nanobubbles) are releasably captured in a biopolymer. The biopolymer disintegrates, dissolves, or otherwise loses its original form in the gastric juice and thereby releases the hydrogen molecules, which enter the surrounding tissues. The biopolymer can be manufactured such that the hydrogen gas is gradually released from the biopolymer matrix as the biopolymer is exposed to the gastric juice. The biopolymer can be manufactured such that it releases $H_2$ molecules over a suitable time period. For example, in some embodiments, the biopolymer may release $H_2$ over a period of 10 minutes, or 15 minutes, or 20 minutes, or 25 minutes, or 30 minutes. In some embodiments, the biopolymer may release $H_2$ over a period of 1 minute, or 2 minutes, or 3 minutes, or 4 minutes, or 5 minutes, or 6 minutes, or 7 minutes, or 8 minutes, or 9 minutes, or 10 minutes. In some embodiments, the biopolymer is configured to slowly release $H_2$ molecules, for example, over a period of more than 10 minutes.

The biopolymer can be any suitable biopolymer, e.g., a food-grade biopolymer matrix that releasably retains hydrogen nanobubbles. The biopolymer matrix can be formed from, for instance, xanthan gum, gelatin, agar-agar, cellulose, or another food-grade biopolymer. In some embodiments, the biopolymer powder, having $H_2$ gas (e.g., nanobubbles) incorporated herein, can additionally include other agents, including magnesium salts (e.g., magnesium oxide), coloring agents, flavoring agents, and/or other ingredients.

Furthermore, in some embodiments, a solid form, including a biopolymer with hydrogen nanobubbles, also includes metallic magnesium. The solid form can include any other ingredients.

The solid form in the powder form, or in another form, can be manufactured as a capsule releasably enclosing the powder therein. The solid form can include other ingredients, non-limiting examples of which include microcrystalline cellulose, xanthan gum, citric acid, maltodextrin, magnesium stearate, gelatin, and a coloring agent.

In some embodiments, the $H_2$-generating or releasing solid form is manufactured such that, upon contact with hydrochloric acid in the gastric environment, it enters into a chemical reaction with hydrochloric acid in the gastric environment. In some embodiments, the $H_2$-generating solid form is manufactured such that it stores hydrogen that is released upon contact of the $H_2$-generating solid form with hydrochloric acid and other liquids in the gastric environment. In some embodiments, when interacting with hydrochloric acid in the gastric environment, the solid form gradually releases the hydrogen into the surrounding environment. For example, the solid form may release $H_2$ over a period of 1 minute, or 2 minutes, or 3 minutes, or 4 minutes, or 5 minutes, or 6 minutes, or 7 minutes, or 8 minutes, or 9 minutes, or 10 minutes. In some embodiments, the solid form may release $H_2$ over a period of from about 1 minute to about 5 minutes. In some embodiments, the solid form may release $H_2$ over a period of more than 10 minutes.

The $H_2$-generating solid forms can include any of the elements that are capable of safely generating $H_2$ upon contact with hydrochloric acid and other liquids (e.g., water) in the gastric juice. Non-limiting examples of such elements include potassium (K), sodium (Na), calcium (Ca), magnesium (Mg), cobalt (Co), manganese (Mn), zinc (Zn) and iron (Fe). For example magnesium (Mg) reacts with hydrochloric acid via the following reaction: $Mg+2HCl=MgCl_2+H_2$. Salts of any one or more of these elements are included in the composition of solid forms in accordance with embodiments of the present disclosure. For instance, in some embodiments, the solid form may have the following composition, which produces about 1.21 mg of $H_2$:

| Component | Amount per tablet (mg) | % |
| --- | --- | --- |
| Mg:KHCO$_3$ (1:8) | 300.00 | 60.0% |
| Mannitol | 133.50 | 36.7% |
| PEG 3350 | 15.00 | 3.0% |
| Silica | 1.50 | 0.3% |
| Total | 500.00 | 100.0% |

In some embodiments, the solid form includes microparticles of metallic magnesium (e.g., about 35 µm, about 36 µm, about 37 µm, about 38 µm, about 39 µm, about 40 µm, about 41 µm, about 42 µm, about 43 µm, about 44 µm, or about 45 µm in size) and/or salts of magnesium. In some embodiments, the solid forms can additionally or alternatively include potassium bicarbonate, sodium bicarbonate, magnesium particles (e.g., about 35 µm, about 36 µm, about 37 µm, about 38 µm, about 39 µm, about 40 µm, about 41 µm, about 42 µm, about 43 µm, about 44 µm, or about 45 µm in size) and other constituents such as, e.g., tartaric acid, inulin, calcium lactate, etc. The solid form can be formulated such that it forms H$_2$ nanobubbles in the subject's gastric juice.

The solid forms can be formulated as dietary supplements and they can include any additives that make them more palatable and at least partially digestible. In some embodiments, the hydrogen-generating composition can include one or more dietary acceptable excipients, non-limiting examples of which in include fillers, binders, disintegrants, lubricants (e.g., magnesium stearate and stearic acid), stabilizers, solubilizers, polymers, glidants, compression aids (e.g., cellulose derivatives) sweeteners, flavoring agents, and coloring agents. In some embodiments, however, the solid forms may not include any additives besides the hydrogen-generating elements and basic ingredients (e.g., microcrystalline cellulose, citric acid, magnesium stearate, gelatin, and coloring).

The solid forms in accordance with the present disclosure can be tablets, pills, powders (e.g., compressed powders), granules, sachets, beads, jell, etc. A solid form can include from about 50 mg to 400 mg of ingredients and release into the gastric juice about 0.5 mg to 4 mg of molecular hydrogen.

In some embodiments, the solid form is in the form of a capsule having an H$_2$-generating powder releasably encapsulated therein. The powder can include magnesium oxide in the amount of from about 1 mg to about 20 mg, or from about 5 mg to about 15 mg, or from about 5 mg to about 10 mg.

The solid form can be of any suitable shape, including an oblong, oval, or round shape that facilitates swallowing. The solid form can have any other shape, as the described embodiments are not limited in this respect.

The solid forms in accordance with embodiments of the present disclosure may be manufactured using conventional techniques for generating tablets, pills, or other solid dosage forms known in the art, such as, e.g., direct compression, wet granulation, dry granulation or extrusion/melt granulation, etc. The solid form can be monolithic. In embodiments in which the solid forms are in the form of capsules, the active, H$_2$-producing ingredients are encapsulated within a shell that dissolves and/or disintegrates upon contact with the fluids within the subject's gastrointestinal tract, after the solid form is swallowed.

In various embodiments, the H$_2$-producing agents and/or hydrogen-generating solid forms described herein, and the methods of treatment or prevention can include an additional agent, such as one or more of nonsteroidal anti-inflammatory drugs (NSAIDs) (e.g., aspirin, ibuprofen), paracetamol/acetaminophen, expectorants (e.g., guaifenesin), mucolytics, mucokinetics, mucoregulators, antihistamines (e.g., acrivastine, diphenhydramine, cetirizine, fexofenadine, hydroxyzine, levocabastine, levocetirizine, and loratadine), and decongestants (e.g., ephedrine, phenylephrine, pseudoephedrine, and oxymetazoline). In embodiments, the H$_2$-producing agents and/or hydrogen-generating solid forms described herein, and the methods of treatment or prevention obviate the need for administration of the additional agents enumerated above.

In various embodiments, the present invention provides a kit including any one of the H$_2$-producing agents and/or hydrogen-generating solid forms described herein. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g., GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

This invention is further illustrated by the following non-limiting examples.

EXAMPLES

Example 1: Individual Patient Response to Ingestible Solid Forms for Prevention and Treatment of Viral Infections Patient #1:

A 57-year old female subject started experiencing flu symptoms. The subject experienced a severe headache, high fever, muscle cramps and running nose. She was administered eight hydrogen-generating pills, such that two pills were taken every two hours. After about 12 hours from the start of taking the hydrogen-generating pills, the flu symptoms subsided, and the subject was able to sleep well without taking any cold/flu medication. In the morning next day, the subject surprisingly did not experience any symptoms. She took additional two hydrogen-generating pills, and her symptoms never returned. Total consumption of molecular hydrogen by this subject was about 80-100 mL (6.64-8.3 mg).

The hydrogen-generating pills used were "AquaActive" (Dibal LLC, San Diego, Calif.), which include microparticles of metallic magnesium and salts of magnesium. When dissolved in a solution of water or hydrochloric acid (gastric juice), each of the hydrogen-generating pills produces from about 10 mL (0.83 mg) to about 14 mL (1.12 mg) of molecular hydrogen.

Patient #2:

A 44-year old female subject, a professional singer, started experiencing symptoms associated with common cold, such as scratchy throat and congested nose. She also started losing her voice. The subject started taking hydrogen-generating pills—two pills every two hours, eight pills total. The next day she took additional two hydrogen-generating pills. The subject's common cold symptoms were reduced significantly after the first 24 hours and she was able to sing at a concert only two days after the first onset of the common cold symptoms. Total consumption of molecular hydrogen by this subject is estimated to be 80-100 mL (6.64-8.30 mg).

The hydrogen-generating pills were "AquaActive" (Dibal LLC), which include microparticles of metallic magnesium and salts of magnesium. When dissolved in a solution of water or hydrochloric acid (gastric juice), each of the hydrogen-generating pills produces from about 10 mL (0.83 mg) to about 14 mL (1.16 mg) of molecular hydrogen.

Patient #3:

An 18-year old male subject started experiencing common cold-like symptoms in the afternoon. He had scratchy throat, running nose, and light fever. In the evening of that day he was administered two hydrogen-generating pills, and then two more hydrogen-generating pills after two hours. The subject was administered two more hydrogen-generating pills in the morning of the next day, such that the subject has taken the total of 6 pills. The subject responded robustly to the therapy—the common cold symptoms were gone at the end of the second day after the beginning of the therapy. Total consumption of molecular hydrogen is estimated to be 60-70 mL (4.98-5.81 mg).

The hydrogen-generating pills were "HyMag60" (Mag and Bio Dynamics, Inc.), which include powder of microparticles of metallic magnesium and salts of magnesium produced by Nano $H_2$ Minus, Inc. (Henderson, Nev.). This microparticles product is manufactured as described in U.S. Pat. No. 8,852,660, which is incorporated herein by reference in its entirety. Each hydrogen-generating pill comprises about 100 mg of the microparticles product and releases about 10 mL (0.83 mg) of $H_2$ in the gastric juice. In some embodiments, a hydrogen-generating pill releases from about 10 mL (0.83 mg) to about 14 mL (1.16 mg) of $H_2$ in the gastric juice.

Patient #4

A 52-year old female subject, while visiting her family, started experiencing flu symptoms such as headache, chills and muscle cramps. This subject was taking hydrogen-generating pills at a regimen of one pill a day. The subject was administered hydrogen-generating pills within about an hour after the onset of the flu symptoms. She took two hydrogen-generating pills three times, every two hours. Thus, she consumed total eight pills, which corresponds to about 80 mL (6.64 mg) of consumed $H_2$. The subject's flu symptoms subsided dramatically after the last two pills were taken, and the subject was completely flu-symptoms-free at the end of the second day after the first onset of the symptoms. Total consumption of $H_2$ is estimated to be 80-100 mL (6.64-8.30 mg). Notably, the subject's family (whom she visited), including four other adults and three children under 18 years old, all had flu for about 10 days The hydrogen-generating pills were "HyMag60" (Mag and Bio Dynamics, Inc.), which include microparticles of metallic magnesium and salts of magnesium produced by Nano $H_2$ Minus, LLC. When consumed, each hydrogen-generating pill produces from about 10 mL (0.83 mg) to about 14 mL (1.16 mg) of molecular hydrogen.

Patient #5:

A 63-year male old subject was on an airplane flight for about 2.5 hours, and a fellow passenger was coughing throughout the entirety of the duration of the flight. After the subject departed the plane, he started experiencing common cold symptoms, such as a headache and body aches, with the symptoms quickly escalating. He was administered two True Nano $H_2$ capsules produced by $H_2$ universe, LLC. Each capsule comprises about 12 mL (1.00 mg) of $H_2$ releasably stored in a biopolymer of Real $H_2$ powder manufactured by DOO Hydrogen MG (Serbia). This powder is hydrogen storage, and 200 mg of powder contains about 1 mg of molecular hydrogen that corresponds to about 12 mL of $H_2$. On the same day, the subject then took four more of the capsules—at a dose of two capsules with an interval of about 2 hours. In the morning the next day, the subject did not experience any of the common cold symptoms, and he additionally consumed two capsules to complete the course of the treatment.

None of the patients exhibited any side effects of the treatment.

Example 2: Assessment of Efficacy of Ingestible Hydrogen-Generating Solid Forms for Treatment of Symptoms of Common Cold In this example, 34 adult subjects participated in a study over a period of eight years, and 205 events of conditions consistent with common cold were assessed, with an average of 6 events per subject.

Each of the 34 subjects was instructed regarding relevant common cold symptoms, and the common cold symptoms were self-diagnosed by the subjects at each of the events. If an event was a suspected allergy or flu, such an event was not included in the common cold study. In each of the events, a subject was administered hydrogen-generating pills at a dose that generated about 20 mL (1.66 mg) of $H_2$ upon consumption, within 24 to 48 hours of the onset of the symptoms of common cold. The hydrogen-generating pills were administered to the subject as the following regimens: 1) 20 mL (1.66 mg) (a unit dose); 2) 40 mL (3.32 mL) (one dose, followed by another dose after about 2 hours); 3) 60 mL (4.98 mg) (three doses with intervals of about 2 hours from one another); and 4) 80 mL (6.64 mg) (four doses with an interval of about 2 hours from one another).

In each of the events, it was recorded when the common cold symptoms first started and when they subsided. The results of the study are shown in FIG. 1. According to the analysis of the obtained data, as shown in FIG. 1, the probability of symptoms of common cold decreased by about 10 times after the subject was administered the $H_2$-generating pills that generated about 80 mL (6.64 mg) of $H_2$ in the subject's body. The FIG. 1 shows the probability of common cold symptoms after 48 hours from the onset of the first symptoms, depending on the amount of hydrogen taken from the moment of the first symptoms within 8 hours. Hydrogen delivery was carried out by the hydrogen-generating pills. The probability of the common cold symptoms after 48 hours decreases dramatically, such that the symptoms subsided significantly (the probability is smaller than 10%) after the subject has received about 80 mL (6.64 mg) of $H_2$ within 8 hours. No side effects of the treatment were observed.

Example 3: Assessment of Efficacy of Ingestible Hydrogen-Generating Solid Forms for Treatment of Symptoms of Influenza Further, influenza (flu) statistics was collected from 12 adult subjects over a period of eight years, and 114 events with symptoms consistent with the flu were assessed. Each of the 34 subjects was instructed regarding relevant flu symptoms, and the flu symptoms were self-diagnosed by the subjects at each of the events. If an event was a suspected allergy or common cold, such an event was not included in the flu study. Within 24 to 48 hours of the symptoms of the disease, the participant was given pills which, when consumed, produced molecular hydrogen. In each of the events, a subject was administered hydrogen-generating pills at a dose that generated about 20 mL (1.66 mg) of $H_2$ upon consumption, within 24 to 48 hours of the onset of the symptoms of common cold. The hydrogen-generating pills were administered to the subject as the following regimens: 1) 20 mL (1.66 mg); 2) 40 mL (3.32 mg) (one dose, followed by another dose after about 2 hours); 3) 60 mL (4.98 mg) (three doses with intervals of about 2 hours from one another); and 4) 80 mL (6.64 mg) (four doses with an interval of about 2 hours from one another).

In each of the events, it was recorded when the flu symptoms first started and when they subsided. The results of the study are shown in FIG. 1. As shown in FIG. 1, the probability of symptoms of flu decreased by about 9 times after the subject was administered the $H_2$-generating pills that generated about 80 mL of $H_2$ in the subject's body. The FIG. 1 shows the probability of flu symptoms after 48 hours from the onset of the first symptoms, depending on the amount of hydrogen taken from the moment of the first symptoms within 8 hours. Hydrogen delivery was carried out by the hydrogen-generating pills The probability of the flu symptoms after 48 hours decreases dramatically, such that the symptoms subsided significantly (the probability is smaller than 10%) after the subject has received about 80 mL (6.64 mg) of $H_2$ within 8 hours. No side effects of the treatment were observed.

Since other modifications and changes varied to fit particular operating requirements and environments will be apparent to those skilled in the art, the invention is not considered limited to the examples chosen for purposes of disclosure, and covers all changes and modifications which do not constitute departures from various embodiments, or combinations of the embodiments, of the invention.

EQUIVALENTS

While the present disclosure has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not patentable in view of such publications.

As used herein, all headings are simply for organization and are not intended to limit the disclosure in any manner. The content of any individual section may be equally applicable to all sections.

What is claimed is:

1. A method of treating symptoms of a viral infection, comprising:
    administering a plurality of ingestible hydrogen-generating solid forms to a subject experiencing an onset of one or more of symptoms of the viral infection, wherein:
    the administering occurs within 24 hours of the onset of the symptoms,
    the viral infection is selected from influenza and common cold,
    the symptoms of the viral infection are selected from one or more of fever, headache, sore throat, nasal congestion, cough, and myalgia,
    each of the plurality of solid forms is configured to release at least 0.83 mg of molecular hydrogen upon exposure to the gastric juice of the subject,
    each of the plurality of solid forms is administered in the absence of pre-administration dilution in water or other liquid, and
    two solid forms of the plurality of solid forms are administered every two hours at least four times such that a total amount of molecular hydrogen administered to the subject is at least 6.6 mg.

2. The method of claim 1, wherein the method generates at least 10 mL of molecular hydrogen upon exposure to the gastric juice of the subject.

3. The method of claim 1, wherein each of the plurality of solid forms is capable of generating at least 1.2 mg of molecular hydrogen.

4. The method of claim 1, wherein each of the plurality of solid forms is capable of generating at least 1.6 mg of molecular hydrogen.

5. The method of claim 1, wherein the plurality of solid forms are administered to deliver from about 6.6 mg to about 8.5 mg of molecular hydrogen to the subject.

6. The method of claim 1, wherein the plurality of solid forms are administered to the subject in a dry form.

7. The method of claim 1, comprising reducing a probability of the symptoms of the viral infection by at least 50% after 48 hours of the beginning of the administration of at least one of the hydrogen-generating solid forms.

8. The method of claim 1, wherein the treating of the symptoms of the viral infections comprises treating Multiple Organ Dysfunction Syndrome.

9. The method of claim 1, wherein the symptoms further comprise an acute upper respiratory infection.

10. The method of claim 1, wherein the symptoms further comprise one or more of those of Table 1.

11. The method of claim 1, wherein a solid form of the solid forms comprise a pill, tablet, capsule, powder, or granule.

* * * * *